United States Patent
Sinclair et al.

(10) Patent No.: US 11,318,168 B2
(45) Date of Patent: May 3, 2022

(54) HUMAN TISSUE DERIVED COMPOSITIONS AND USES THEREOF

(71) Applicant: Osiris Therapeutics, Inc., Columbia, MD (US)

(72) Inventors: Steven Michael Sinclair, Ellicott City, MD (US); Alla Danilkovitch, Columbia, MD (US); Malathi Sathyamoorthy, Ellicott City, MD (US); Jin-Qiang Kuang, Glenelg, MD (US); Sandeep Dhall, Elkridge, MD (US); Yishan Liu, Doylestown, PA (US); Anthony John Melchiorri, Ellicott City, MD (US); Matthew Robert Moorman, Chestertown, MD (US); Mena Schiano Lo Moriello, Silver Spring, MD (US); Anne Allgood Lerch, Annapolis, MD (US)

(73) Assignee: OSIRIS THERAPEUTICS, INC., Columbia, MD (US)

( * ) Notice: Subject to any disclaimer, the term of this patent is extended or adjusted under 35 U.S.C. 154(b) by 0 days.

(21) Appl. No.: 15/631,707

(22) Filed: Jun. 23, 2017

(65) Prior Publication Data
US 2017/0368105 A1 Dec. 28, 2017

Related U.S. Application Data

(60) Provisional application No. 62/354,466, filed on Jun. 24, 2016.

(51) Int. Cl.
*A61K 35/50* (2015.01)
*A61K 35/51* (2015.01)
(Continued)

(52) U.S. Cl.
CPC ............ *A61K 35/50* (2013.01); *A61K 9/0014* (2013.01); *A61K 9/0019* (2013.01);
(Continued)

(58) Field of Classification Search
CPC .......... A61K 35/50; A61K 9/19; A61K 35/51; A61K 9/0014; A61K 9/0019;
(Continued)

(56) References Cited

U.S. PATENT DOCUMENTS

| 6,962,775 B2 | 11/2005 | Kuri-Harcuch et al. |
| 8,231,908 B2 | 7/2012 | Kinoshita et al. |

(Continued)

FOREIGN PATENT DOCUMENTS

| WO | WO 97/45009 | 12/1997 |
| WO | WO 2008/021391 | 2/2008 |

(Continued)

OTHER PUBLICATIONS

Rodriguez-Ares et al. "Effects of lyophilization on human amniotic membrane" Acta Opthalmologica (Year: 2009).*

(Continued)

*Primary Examiner* — Blaine Lankford
*Assistant Examiner* — Lauren K Van Buren
(74) *Attorney, Agent, or Firm* — Norton Rose Fulbright US LLP

(57) ABSTRACT

Disclosed are compositions comprising a non-homogenized chorionic matrix, a homogenized amniotic matrix and a homogenized UC (UC) matrix, wherein the non-homogenized chorionic matrix comprises viable cells. Disclosed are methods of making the compositions disclosed herein comprising preparing a non-homogenized chorionic matrix, preparing a homogenized amniotic matrix, preparing a homogenized UC matrix, and combining the non-homogenized chorionic matrix, the non-homogenized chorionic (Continued)

A.

B.

C.

matrix, and the homogenized UC matrix. Disclosed are methods of treating a tissue injury or chronic pain comprising administering any of the disclosed compositions to an area of a subject comprising a tissue injury.

12 Claims, 9 Drawing Sheets

(51) Int. Cl.

| | |
|---|---|
| *A01N 1/02* | (2006.01) |
| *A61K 9/00* | (2006.01) |
| *A61K 9/06* | (2006.01) |
| *A61K 9/19* | (2006.01) |
| *A61K 35/33* | (2015.01) |
| *A61P 19/00* | (2006.01) |
| *A61P 19/04* | (2006.01) |
| *A61P 17/02* | (2006.01) |
| *A61P 29/00* | (2006.01) |
| *A61P 19/10* | (2006.01) |
| *A61P 19/02* | (2006.01) |
| *A61L 27/36* | (2006.01) |
| *A61L 27/38* | (2006.01) |
| *A61L 26/00* | (2006.01) |

(52) U.S. Cl.
CPC .............. *A61K 9/0024* (2013.01); *A61K 9/06* (2013.01); *A61K 9/19* (2013.01); *A61K 35/33* (2013.01); *A61K 35/51* (2013.01); *A61L 26/0057* (2013.01); *A61L 27/3604* (2013.01); *A61L 27/3834* (2013.01); *A61P 17/02* (2018.01); *A61P 19/00* (2018.01); *A61P 19/02* (2018.01); *A61P 19/04* (2018.01); *A61P 19/10* (2018.01); *A61P 29/00* (2018.01)

(58) Field of Classification Search
CPC ........ A61K 9/0024; A61K 9/06; A61K 35/33; A61L 27/3834; A61L 26/0057; A61L 27/3604; A61P 17/02; A61P 19/00; A61P 19/02; A61P 19/04; A61P 19/10; A61P 29/00

See application file for complete search history.

(56) References Cited

U.S. PATENT DOCUMENTS

| 9,956,248 | B2 | 5/2018 | Tom et al. | |
|---|---|---|---|---|
| 2008/0069895 | A1 | 3/2008 | Liu et al. | |
| 2008/0131522 | A1* | 6/2008 | Liu ........................ | A61K 35/44 424/583 |
| 2012/0276581 | A1* | 11/2012 | Arav ..................... | A01N 1/0221 435/34 |
| 2014/0301986 | A1* | 10/2014 | Tom ........................ | A61P 43/00 424/93.7 |
| 2015/0010506 | A1* | 1/2015 | Jansen ................... | A61K 38/22 424/85.7 |
| 2015/0010610 | A1 | 1/2015 | Tom et al. | |
| 2015/0231183 | A1 | 8/2015 | Peterson et al. | |
| 2015/0342998 | A1* | 12/2015 | Tseng ..................... | A61K 35/28 424/443 |
| 2016/0030635 | A1 | 2/2016 | Bhatia et al. | |

FOREIGN PATENT DOCUMENTS

| WO | WO-2011/031489 A2 | 3/2011 |
|---|---|---|
| WO | WO-2011/103446 A1 | 8/2011 |
| WO | WO-2016/033041 A1 | 3/2016 |

OTHER PUBLICATIONS

U.S. Appl. No. 62/354,466, filed Jun. 24, 2016, Sinclair et al. (Osiris Therapeutics, Inc.).
PCT/US2017/039075, Jun. 23, 2017, Sinclair et al. (Osiris Therapeutics, Inc.).
Parolini, O. et al., Concise Review: Isolation and Characterization of Cells from Human Term Placenta: Outcome of the First International Workshop on Placenta Derived Stem Cells. Stem Cells. 2008; 26(2): 300-11.
Portmann-Lanz, C.B. et al., Placental Mesenchymal Stem Cells as Potential Autologous Graft for Pre- and Perinatal Neuroregeneration. Am J Obstet Gynecol. 2006; 194: 664-73.
Socini, M. et al., Isolation and Characterization of Mesenchymal Cells from Human Fetal Membranes. J Tissue Eng Regen Med. 2007; 1(4): 296-305.
Non Final Rejection dated Mar. 29, 2019 by the USPTO for U.S. Appl. No. 16/229,823, filed Dec. 21, 2018 and published as US-2019-0134099-A1 on May 9, 2019 (Inventor—Steven Michael Sinclair) (24 Pages).
International Search Report and Written Opinion dated Sep. 14, 2017 by the International Searching Authority for International Patent Application No. PCT/US2017/039075, which was filed on Jun. 23, 2017 (Applicant—Osiris Therapeutics, Inc.) (12 pages).
Cooke, et al. "Comparison of cryopreserved amniotic membrane and umbilical cord tissue with dehydrated amniotic membrane/chorion tissue," Journal of Wound Care, 2014, 23(10):465-476.
Duan-Arnold, et al. "Retention of Endogenous Viable Cells Enhances the Anti-Inflammatory Activity of Cryopreserved Amnion," Advances in Wound Care, 2015, 4(9):523-533.
Extended European Search Report issued in corresponding European Patent Application No. 17816324.2, dated Dec. 5, 2019.
Extended European Search Report issued in corresponding European Patent Application No. 17816341.6, dated Dec. 2, 2019.
International Preliminary Report on Patentability dated Dec. 25, 2018 by the International Searching Authority for International Patent Application No. PCT/US2017/039075, which was filed on Jun. 23, 2017 and published as WO 2017/223494 on Dec. 28, 2017 (Inventor—Sinclair et al.; Applicant—Osiris Therapeutics, Inc.; (6 pages).
International Search Report and Written Opinion dated Sep. 25, 2017 by the International Searching Authority for International Patent Application No. PCT/US2017/039123, which was filed on Jun. 23, 2017 (Applicant—Osiris Therapeutics, Inc.) (9 pages).

* cited by examiner

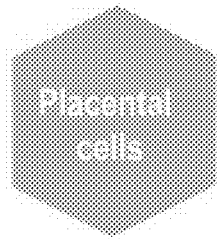
- Cell Source
  - Chorion, non-expanded
  - Optionally: amnion epithelial or stromal

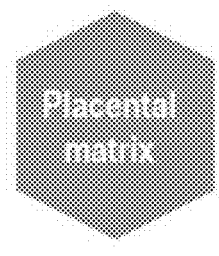
- Matrix Source from same donor
  - Amnion & Umbilical Cord homogenate, contains minimal viable cells

- Viscous Modifier
  - Commercially available components of topical creams/gels (e.g. Methylcellulose or xantham gum)

- Specialized Scaffold
  - Tunable properties
  - Thermally responsive, or adhesive, or mechanically strong

FIG. 2

| Cell Surface Marker | % Positive |
|---|---|
| HLA-ABC | 69.03% |
| CD90 | 71.32% |
| CD73 | 52.92% |
| CD44 | 61.88% |
| HLA-DR | 2.41% |
| CD31 | 0.68% |
| CD34 | 0.92% |
| CD45 | 3.52% |

FIG. 8

HUMAN TISSUE DERIVED COMPOSITIONS AND USES THEREOF

CROSS-REFERENCE TO RELATED APPLICATIONS

This application claims benefit of U.S. Provisional Application No. 62/354,466, filed Jun. 24, 2016, which is hereby incorporated herein by reference in its entirety.

BACKGROUND

The use of placental tissues for burns and other types of wounds originated more than 100 years ago. Placental tissues contain components that are present in skin and other tissues and required for wound healing or tissue regeneration such as extracellular matrix, growth factors, and cells, including MSCs that are responsible for orchestrating the healing process in different tissue types. The effectiveness of placental tissues such as amniotic and chorionic membranes for burns, ocular wounds, orthopedic, and sports medicine surgical applications has been recorded in a number of published reports; however, the use of fresh placental tissues for a variety of indications is limited due to challenges of short shelf-life.

What is needed in the art is a therapeutic product that provides the benefits of placental tissues yet can be applied in flowable forms that is compatible with delivery via injection or minimally invasive techniques such as arthroscopy, endoscopy, or laprascopy. Furthermore, a therapeutic product that contains matrix proteins, growth factors, and viable placental cells that will dynamically respond to the injury and aid in tissue regeneration is desired. Flowable forms of such therapeutics could be used to produce a solid matrix which can be prepared into most shapes and sizes. The methods and materials described herein can provide a solution to such needs.

BRIEF SUMMARY

Disclosed are compositions comprising a non-homogenized chorionic matrix, a homogenized amniotic matrix and a homogenized umbilical cord (UC) matrix, wherein the non-homogenized chorionic matrix comprises viable cells.

Disclosed are compositions comprising a non-homogenized chorionic matrix, a homogenized amniotic matrix and a homogenized UC matrix, wherein the non-homogenized chorionic matrix comprises viable native cells, and wherein the composition further comprises viable, isolated amniotic cells.

Disclosed are methods of making the compositions disclosed herein comprising preparing a non-homogenized chorionic matrix, preparing a homogenized amniotic matrix, preparing a homogenized UC matrix, and combining the non-homogenized chorionic matrix, the homogenized amniotic matrix, and the homogenized UC matrix.

Disclosed are methods of making the compositions disclosed herein comprising preparing a non-homogenized chorionic matrix, preparing a homogenized amniotic matrix, preparing a homogenized UC matrix, and combining the non-homogenized chorionic matrix, the homogenized amniotic matrix, and the homogenized UC matrix further comprising prior to preparing a homogenized amniotic matrix, performing the step of isolating epithelial cells from the amniotic matrix.

Disclosed are methods of making one of the compositions disclosed herein comprising isolating chorionic tissue, isolating amniotic tissue, isolating and deveining UC tissue, rinsing each of the isolated chorionic tissue, isolated amniotic tissue, and deveined UC tissue individually, mincing or digesting the isolated chorionic tissue, combining and homogenizing the isolated amniotic tissue and the deveined UC tissue to form a placental matrix, and combining the minced or digested chorionic tissue with the placental matrix.

Disclosed are methods of making one of the compositions disclosed herein comprising isolating chorionic tissue, isolating amniotic tissue, isolating and deveining UC tissue, rinsing each of the isolated chorionic tissue, isolated amniotic tissue, and deveined UC tissue individually, mincing or digesting the isolated chorionic tissue, combining and homogenizing the isolated amniotic tissue and the deveined UC tissue to form a placental matrix, and combining the minced or digested chorionic tissue with the placental matrix, further comprising isolating epithelial cells from the amniotic tissue prior to combining and homogenizing the isolated amniotic tissue and the deveined UC tissue to form a placental matrix and combining the isolated amniotic epithelial cells.

Disclosed are methods of treating a tissue injury or chronic pain comprising administering any of the disclosed compositions to an area of a subject comprising a tissue injury.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIG. 2 shows bioengineered platform building blocks.

FIG. 8 summarizes the FACS analysis of cells isolated from the non-homogenized viable chorionic component of the compositions.

DETAILED DESCRIPTION

Figure 1A:
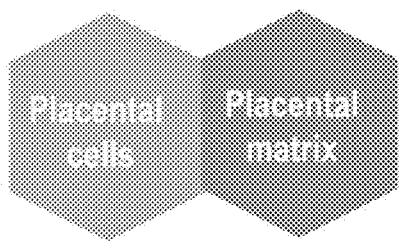
FIGS. 1A, 1B, and 1C are a schematic of the different compositions with their intended uses. A) Injectable—examples of indications are: knee osteoarthritis, plantar fasciitis, achilles tendon repair, critical limb ischemia, plastic procedures, diabetic foot ulcers (DFUs), venous leg ulcers (VLUs), pressure ulcers, pyoderma gangrenosum, epidermolysis bullosa, other wounds, plastic procedures. B) Topical—examples of indications are DFUs, VLUs, pressure ulcers, pyoderma gangrenosum, epidermolysis bullosa, other wounds, plastic procedures; C) Surgical—examples of indications are meniscus repair, disc repair, plastic reconstructions, cartilage repair, surgical adhesion barriers for laprascopic or open procedures in gynecology, urology, bariatrics, or similar fields, and bone repair.
Figure 1B:
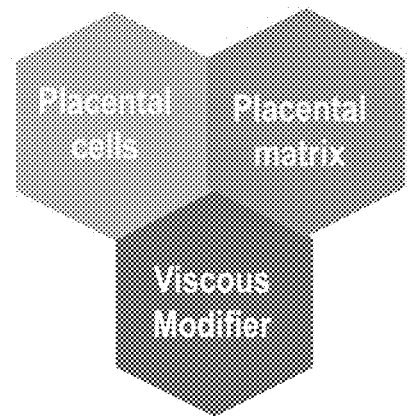
Figure 1C:
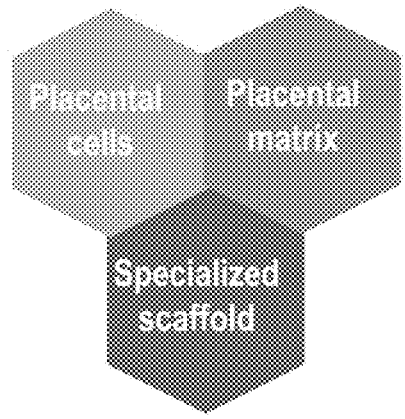
Figure 3:
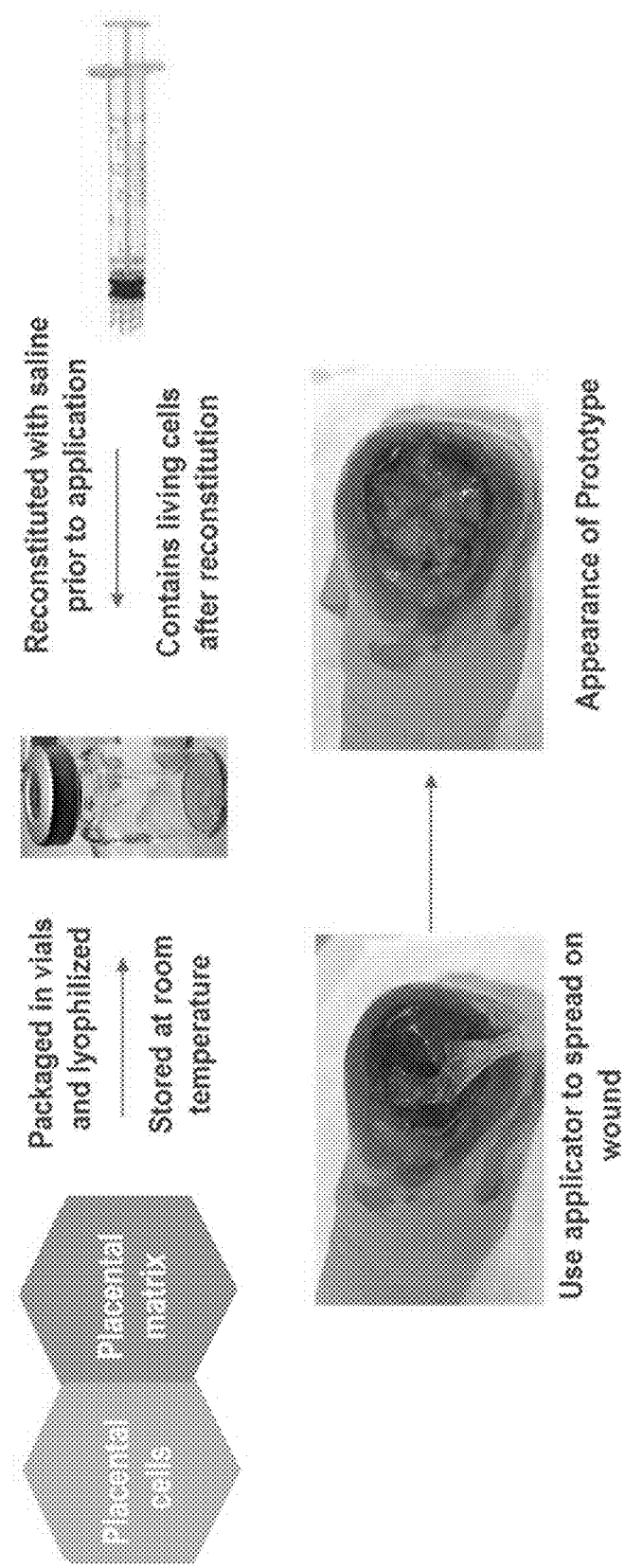
FIG. 3 shows a composition/product for chronic wounds. The composition/product is a lyophilized flowable formulation of chorionic matrix containing viable tissue native cells mixed with umbilical cord and amniotic matrix. The composition/product was stored at room temperature and was reconstituted with saline solution prior to application.
Figure 4:
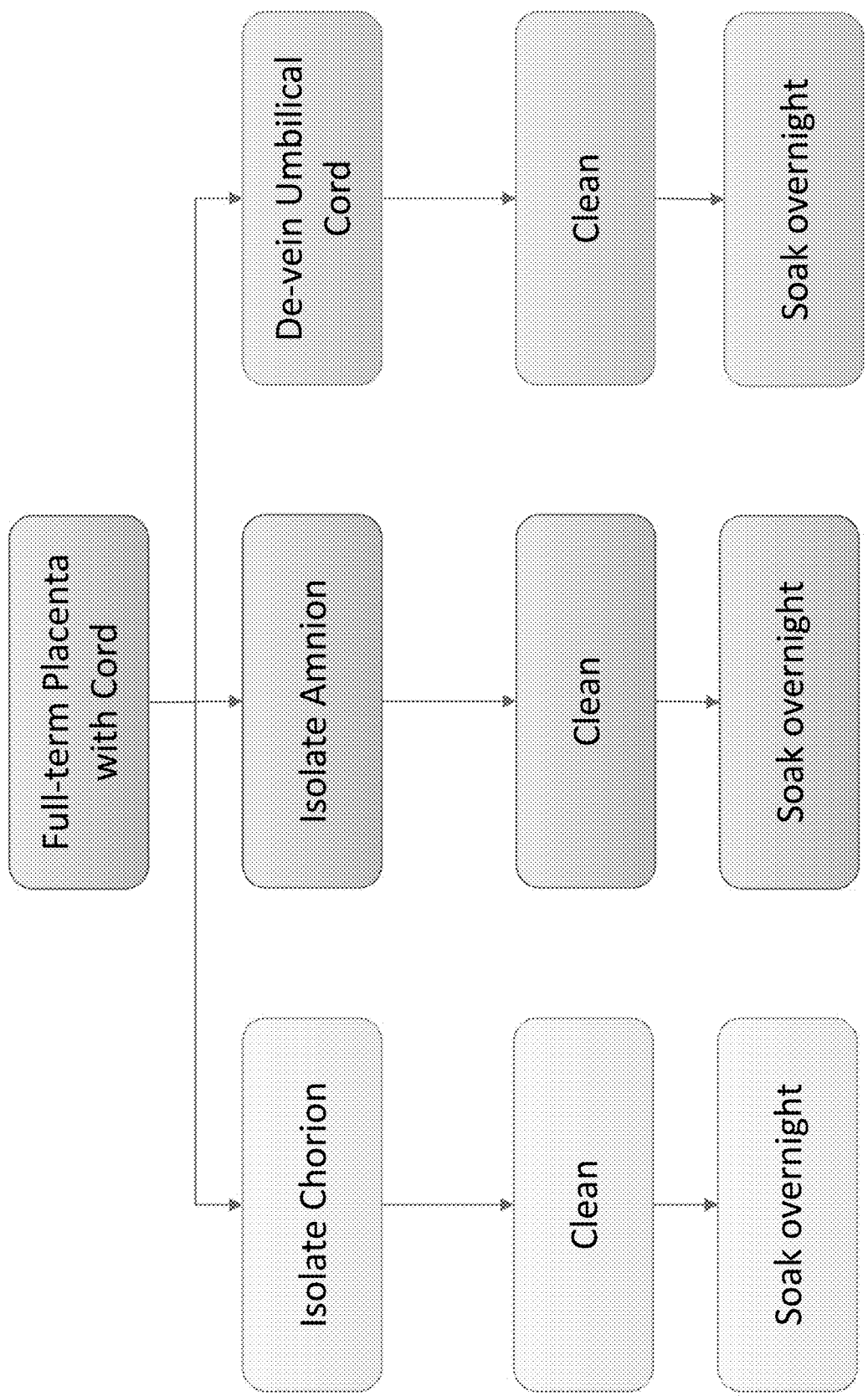
FIG. 4 is a diagram of an example of how to process full-term placenta with UC.
Figure 4:
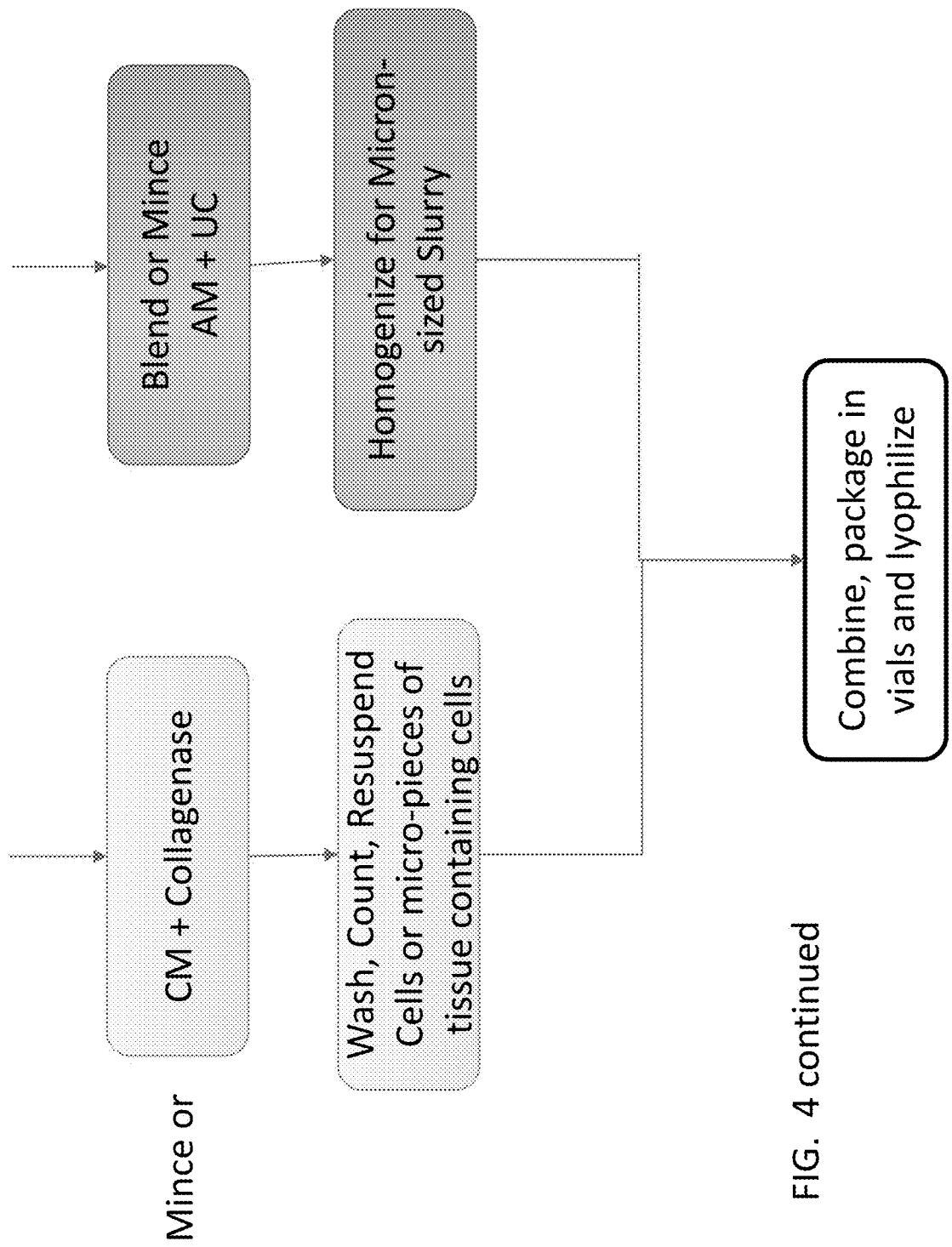

The disclosed method and compositions may be understood more readily by reference to the following detailed description of particular embodiments and the Example included therein and to the Figures and their previous and following description.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

A. Definitions

The phrase "isolated amniotic cells" refers to cells removed or isolated from amniotic tissue prior to homogenization of the amniotic tissue. Isolated amniotic cells can refer to a population of epithelial cells and/or stromal fibroblasts or stromal MSCs with at least 30%, 40%, 50%, 60%, 70%, 80%, 90%, or 95% cell viability. The term "homogenized" means to make substantially similar in size and composition For example, if a portion of a homogenized tissue matrix was removed after homogenization, the overall morphology and macromolecular make up in the portion removed and in the remaining homogenized tissue matrix would be substantially similar in size and composition. For example, a "homogenized amniotic matrix" and "homogenized umbilical cord matrix" can mean that the amnion or umbilical cord samples have been processed to a point that the entire sample is comprised of particles smaller than 1 mm in diameter (hydrodynamic radius of 0.5 mm), and preferably small enough to pass through an 18-gauge needle (inner diameter of 0.838 mm) without requiring significant syringe plunger pressure, as well as soluble factors homogeneously distributed through the sample. In some aspects, a homogenized tissue can be a tissue that has been previously homogenized wherein the homogenized tissue can have particle sizes within the ranges of 10 nm to 1 mm, or preferably 100 µm to 500 µm, 1 µm to 100 µm, 100 nm to 1 µm, or 10 nm to 100 nm. Generally, methods used for homogenization apply more power (energy over time) to the compositions than non-homogenization methods, such as mincing.

"Mincing" means to cut to make similar in size and composition; however mincing generally results in less uniformity and larger particles than homogenization or homogenized tissue (e.g. range of particle sizes is broader than the range of particle sizes of a homogenized tissue). "Minced tissue" refers to tissue that has been minced and is generally less uniform and has larger average particle sizes than homogenized tissue.

"Selective depletion of immunogenicity" or "selective depletion of immunogenic cells or factors" or "selective depletion" means a tissue (e.g. chorion, amnion, UC) that retains live therapeutic cells and/or retains therapeutic efficacy for the treatment of tissue injury yet is free, substantially free, or depleted of at least one immune or immunogenic cell type (e.g. lymphocytes, macrophages, trophoblasts, and/or vascular-tissue derived cells) and/or immunogenic factor that are otherwise present in the native tissue.

It must be noted that as used herein and in the appended claims, the singular forms "a", "an", and "the" include plural reference unless the context clearly dictates otherwise. Thus, for example, reference to "a chorionic matrix" includes a plurality of such chorionic matrices, reference to "the chorionic matrix" is a reference to one or more chorionic matrices and equivalents thereof known to those skilled in the art, and so forth.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

B. Compositions

Disclosed are compositions comprising a non-homogenized chorionic matrix, a homogenized amniotic matrix and a homogenized umbilical cord (UC) matrix, wherein the non-homogenized chorionic matrix comprises viable cells.

Disclosed are compositions comprising a non-homogenized chorionic matrix, a homogenized amniotic matrix and a homogenized UC matrix, wherein the non-homogenized chorionic matrix comprises viable cells and further comprising viable, isolated amniotic cells. Thus, disclosed are compositions comprising a non-homogenized chorionic matrix, isolated, viable amniotic epithelial cells, a homogenized amniotic matrix and a homogenized UC matrix, wherein the non-homogenized chorionic matrix comprises viable cells. In some aspects, the isolated, viable amniotic epithelial cells are from the same amniotic tissue as the homogenized amniotic matrix. In some aspects, the isolated, viable amniotic epithelial cells are from a different amniotic tissue as the homogenized amniotic matrix.

Chorionic matrix is gently prepared in order to preserve cell viability of the chorionic cells. Thus, the chorionic matrix is a non-homogenized chorionic matrix. In some aspects, non-homogenized chorionic matrix can be minced.

In some aspects, non-homogenized chorionic matrix can comprise native, viable cells. In some aspects, the native, viable cells have not been culturally expanded. In some aspects, the native, viable cells have never been removed from the chorionic matrix. In some aspects, non-homogenized chorionic matrix can comprise viable cells that have not been culturally expanded. In some aspects, non-homogenized chorionic matrix is not substantially devitalized. Non-homogenized chorionic matrix can comprise some dead cells. In some aspects, non-homogenized chorionic matrix can comprise greater than 50%, 60%, 70%, 80%, 90%, 95% viable cells. In some aspects, the non-homogenized chorionic matrix can comprise greater than or equal to 100,000 viable cells/ml. In some aspects, the ratio of viable chorionic cells to all other nonviable cells in the composition can be 5:1, 2:1, 1:1, 1:2, 1:5, 1:10, 1:20, 1:30, 1:40, 1:50, 1:60, 1:70, 1:80, 1:90 or 1:100. In some aspects amniotic cells are isolated from the amniotic tissue prior to homogenizing or mincing and then the isolated amniotic cells are added back to the disclosed compositions. Thus, when isolated amniotic cells are added back into the composition, the ratio of viable chorionic cells to all other nonviable cells is higher because there are less nonviable cells because the amniotic cells can be still viable after being isolated and combined back into the composition.

In some aspects, the homogenized amniotic matrix and/or the homogenized UC matrix are not decellularized. In some aspects, the homogenized amniotic matrix and/or the homogenized UC matrix are devitalized. Thus, the homogenized amniotic matrix and/or the homogenized UC matrix can comprise non-viable cells.

In some aspects, the homogenized amniotic matrix and homogenized UC matrix can be derived from the same donor. In some aspects, the non-homogenized chorionic matrix and homogenized amniotic matrix can be derived from the same donor. In some aspects, the non-homogenized chorionic matrix and homogenized UC matrix can be derived from the same donor. In some aspects, the non-homogenized chorionic matrix and homogenized amniotic matrix and homogenized UC matrix can be derived from the same donor. In some aspects, each of the non-homogenized chorionic matrix and homogenized amniotic matrix and homogenized UC matrix can be derived from different donors. In some aspects, at least one of the non-homogenized chorionic matrix and homogenized amniotic matrix and homogenized UC matrix is from a different donor than the other two matrices.

In some aspects, the disclosed compositions can comprise viable chorionic stem cells, fibroblasts, epithelial cells or a combination thereof.

In some aspects, the homogenized UC matrix comprises de-veined UC tissue.

In some aspects, the disclosed compositions can be cryopreserved. Thus, disclosed are compositions comprising a non-homogenized chorionic matrix, a homogenized amniotic matrix and a homogenized UC (UC) matrix, wherein the non-homogenized chorionic matrix comprises viable cells and further comprising a cryopreservation solution. In some aspects, a cryopreservation solution can contain one or more non-cell permeating cryopreservatives. Examples of non-cell permeating cryopreservatives, include but not limited to, polyvinyl pyrrolidione, a hydroxyethyl starch, a polysaccharide, a monosaccharide, an alginate, trehalose, raffinose, dextran, human serum albumin, Ficoll, lipoproteins, polyvinyl pyrrolidone, hydroxyethyl starch, autologous plasma or a mixture thereof. In some aspects, the cryopreservative does not contain DMSO or glycerol. Further, a cryopreservation solution can contain serum albumin or other suitable proteins to stabilize the disclosed compositions during the freeze-thaw process and to reduce the damage to cells, thereby maintaining viability. In some aspects, a cryopreservation solution can contain a physiological solution, such as a physiological buffer or saline, for example phosphate buffer saline. In some aspects, a cryopreservation solution can comprise a lyoprotectant, such as trehalose or trehalose in combination with one or more antioxidants.

In some aspects, disclosed are compositions comprising a non-homogenized chorionic matrix, a non-homogenized amniotic matrix and a homogenized UC matrix, wherein the non-homogenized chorionic matrix comprises viable cells. Also disclosed are compositions comprising a non-homogenized chorionic matrix, a non-homogenized amniotic matrix and a homogenized UC matrix, wherein the non-homogenized chorionic matrix comprises viable cells and wherein the composition further comprises viable, isolated amniotic cells. In some aspects, non-homogenized amniotic matrix can be minced.

In some aspects, disclosed are compositions comprising a non-homogenized chorionic matrix, a homogenized amniotic matrix and a non-homogenized UC matrix, wherein the non-homogenized chorionic matrix comprises viable cells. Also disclosed are compositions comprising a non-homogenized chorionic matrix, a homogenized amniotic matrix and a non-homogenized UC matrix, wherein the non-homogenized chorionic matrix comprises viable cells and wherein the composition further comprises viable, isolated amniotic cells. In some aspects, non-homogenized UC matrix can be minced.

In some aspects, disclosed are compositions comprising a non-homogenized chorionic matrix, a non-homogenized amniotic matrix and a non-homogenized UC matrix, wherein the non-homogenized chorionic matrix comprises viable cells. Also disclosed are compositions comprising a non-homogenized chorionic matrix, a non-homogenized amniotic matrix and a non-homogenized UC matrix, wherein the non-homogenized chorionic matrix comprises viable cells and wherein the composition further comprises viable, isolated amniotic cells. In some aspects, non-homogenized amniotic matrix and/or the non-homogenized UC matrix can be minced.

Thus, in some aspects, the disclosed compositions can comprise a variety of components that include a non-homogenized chorionic matrix, a non-homogenized or homogenized amniotic matrix, a non-homogenized or homogenized UC matrix, wherein the non-homogenized chorionic matrix comprises viable cells. In some aspects, the disclosed compositions can comprise a variety of components that include a non-homogenized chorionic matrix, a non-homogenized or homogenized amniotic matrix, a non-homogenized or homogenized UC matrix, wherein the non-homogenized chorionic matrix comprises viable cells and wherein the composition further comprises viable, isolated amniotic cells.

In some aspects, the disclosed compositions can be lyophilized.

1. Compositions with a Viscous Modifier

In some aspects, a viscous modifier can be added to any of the disclosed compositions. Thus, disclosed are compositions comprising a non-homogenized chorionic matrix, a homogenized amniotic matrix, a homogenized UC matrix and a viscous modifier, wherein the non-homogenized chorionic matrix comprises viable cells.

In some aspects, the viscous modifier can be hyaluronic acid, methylcellulose, carboxymethylcellulose, xanthum gum, pluronics, thermally responsive polymers (e.g. PNIPAAM) and proteins, fibronectins, laminins, collagens, chitosan, or chondroitin sulfate.

In some aspects, a viscous modifier allows or helps the disclosed compositions to be formulated as a cream, gel, oil, ointment, or lotion.

2. Compositions with a Scaffold

In some aspects, a scaffold can be added to any of the disclosed compositions. Thus, disclosed are compositions comprising a non-homogenized chorionic matrix, a homogenized amniotic matrix, a homogenized UC matrix and a scaffold, wherein the non-homogenized chorionic matrix comprises viable cells.

In some aspects, the scaffold can be natural or synthetic. In some aspects, scaffold is a natural or synthetic polymer. In some aspects, the scaffold can be derived from skin, hyaline cartilage, meniscus, intervertebral disc, or bone. In some aspects, any type of tissue can be used as a scaffold. For example, tissue can be made into a matrix by mincing or homogenizing the tissue. In some aspects, placenta can be used as a scaffold.

In some aspects, a scaffold helps provide a matrix or structure for the disclosed compositions wherein the compositions can then be used in surgical applications. In some aspects, scaffolds can help give the compositions a specific shape.

3. Pharmaceutical Compositions

Disclosed are pharmaceutical compositions comprising any one of the compositions disclosed herein and a pharmaceutically acceptable carrier.

C. Methods of Making Compositions

Disclosed are methods of making the compositions disclosed herein comprising preparing a non-homogenized chorionic matrix, preparing a homogenized amniotic matrix, preparing a homogenized UC matrix, and combining the non-homogenized chorionic matrix, the homogenized amniotic matrix, and the homogenized UC matrix into a single composition. In some aspects, the methods of making the compositions disclosed herein further comprises combining viable, isolated amniotic cells to the composition.

Disclosed are methods of making the compositions disclosed herein comprising preparing a non-homogenized chorionic matrix, preparing a homogenized amniotic matrix, preparing a homogenized UC matrix, and combining the non-homogenized chorionic matrix, the non-homogenized chorionic matrix, and the homogenized UC matrix, further comprising adding a viscous modifier. Any of the viscous modifiers disclosed herein can be used.

Disclosed are methods of making the compositions disclosed herein comprising preparing a non-homogenized chorionic matrix, preparing a homogenized amniotic matrix, preparing a homogenized UC matrix, and combining the non-homogenized chorionic matrix, the non-homogenized chorionic matrix, and the homogenized UC matrix, further comprising adding a scaffold. Additional scaffolds can be natural or synthetic. Suitable scaffolds include, but are not limited to, for example, allografts, autografts, xenografts, ceramics, bioglass, calcium sulphate, demineralized bone matrix, coral, collagen, graft composites, chondronic scaffolds, synthetic scaffolds of all types, natural/biological scaffolds of all types and the like (e.g., calcium phosphates, hydroxyapatite and tricalcium phosphate, collagen/ceramic composite, PCL, PLLA,PLGA, PEG, PGA, alginates, silk, collagen, dextran gelatin, elastin, agarose, chitosan, hyaluronan, HA-TCP-Collagen, GraftJacket®, Alloderm®, PriMatrix® and others). Types thereof include, but are not limited to, other configurations such as sponges, foams, films, sheets, gels.

The compositions disclosed herein can also be used with a carrier. In some aspects, the compositions disclosed herein can be applied to a carrier. It would be appreciated by one skilled in the art that any suitable biocompatible scaffold or carrier or bone grafting material may be used.

In some aspects, the methods of making the compositions disclosed herein further comprises combining viable, isolated amniotic cells to the composition.

Disclosed are methods of making the compositions disclosed herein comprising preparing a non-homogenized chorionic matrix, preparing a non-homogenized amniotic matrix, preparing a homogenized UC matrix, and combining the non-homogenized chorionic matrix, the non-homogenized amniotic matrix, and the homogenized UC matrix into a single composition. In some aspects, the methods of making the compositions disclosed herein further comprises combining viable, isolated amniotic cells to the composition.

Disclosed are methods of making the compositions disclosed herein comprising preparing a non-homogenized chorionic matrix, preparing a non-homogenized amniotic matrix, preparing a non-homogenized UC matrix, and combining the non-homogenized chorionic matrix, the non-homogenized amniotic matrix, and the non-homogenized UC matrix into a single composition. In some aspects, the methods of making the compositions disclosed herein further comprises combining viable, isolated amniotic cells to the composition.

Disclosed are methods of making the compositions disclosed herein comprising preparing a non-homogenized chorionic matrix, preparing a homogenized amniotic matrix, preparing a non-homogenized UC matrix, and combining the non-homogenized chorionic matrix, the homogenized amniotic matrix, and the non-homogenized UC matrix into a single composition. In some aspects, the methods of making the compositions disclosed herein further comprises combining viable, isolated amniotic cells to the composition.

1. Preparing a Non-Homogenized Chorionic Matrix

Chorionic matrix is gently prepared in order to preserve cell viability of the chorionic cells. Thus, the chorionic matrix is a non-homogenized chorionic matrix. In some aspects, preparing a non-homogenized chorionic matrix can comprise mincing, dicing, chopping, or digesting chorionic tissue to form a non-homogenized chorionic matrix. Preparing a chorionic matrix can result in the chorionic matrices disclosed herein. In some aspects, chorionic matrix comprises only chorionic tissue and no other placental tissue or UC tissue.

In some aspects, immunogenic cells or factors can be removed from the non-homogenized chorionic matrix. In some aspects, non-homogenized chorionic matrix can be made immunocompatible by selectively depleting it of functional immunogenic cells. A chorion, chorionic tissue, or chorionic matrix can be made immunocompatible by selectively removing immunogenic cells from the chorion relative to therapeutic cells. For example, immunogenic cells can be removed by depleting or devitalizing the immunogenic cells or by purification of chorionic tissue there from.

In some aspects, the chorionic tissue can be made immunocompatible by selectively depleting trophoblasts, for example, by removal of the trophoblast layer.

In some aspects, the chorionic tissue can be made immunocompatible by selective depletion of functional+macrophages, optionally resulting in depleteion of TNFα upon stimulation, or a combination thereof.

In some aspects, the chorionic tissue can be made immunocompatible by selective depletion of maternal blood cells.

In some aspects, the chorionic tissue can be made immunocompatible by selective depletion of functional macrophages, trophoblasts, and vascularized tissue-derived cells.

In some aspects, the chorionic tissue can be made immunocompatible by selective depletion of trophoblasts and/or macrophages, optionally resulting in depletion of TNFα upon stimulation.

i. Trophoblast Removal

In some aspects, trophoblasts are selectively depleted or removed from the chorionic tissue. Surprisingly, trophoblast depleted chorionic tissue has one or more of the following superior features: is substantially non-immunogenic; and provides enhanced therapeutic efficacy.

Trophoblasts can be removed in any suitable manner which substantially diminishes the trophoblast content of the chorionic tissue. Optionally, the trophoblasts are selectively removed or otherwise removed without eliminating a substantial portion of one or more therapeutic components from the chorionic tissue (e.g. MSCs, chorionic factors, etc). Optionally, a majority (e.g. substantially all) of the trophoblasts are removed.

One method of removing trophoblasts comprises treating the chorionic tissue with a digestive enzyme such as dispase (e.g. dispase II) and separating the trophoblasts from the chorionic tissue. Optionally, the step of separating comprises mechanical separation such as peeling or scraping. Optionally, scraping comprises scraping with a soft instrument such as a finger.

One method of removing trophoblasts comprises treating the chorionic membrane with dispase for about 30 to about 45 minutes separating the trophoblasts from the chorionic tissue. Optionally, the dispase is provided in a solution of about less than about 1% (e.g. about 0.5%). Optionally, the step of separating comprises mechanical separation such as peeling or scraping. Optionally, scraping comprises scraping with a soft instrument such as a finger.

Useful methods of removing trophoblasts from a placenta (e.g. chorion) are described by Portmann-Lanz et al. ("Placental mesenchymal stem cells as potential autologous graft for pre- and perinatal neuroregeneration"; American Journal of Obstetrics and Gynecology (2006) 194, 664-73), ("Isolation and characterization of mesenchymal cells from human fetal membranes"; Journal Of Tissue Engineering And Regenerative Medicine 2007; 1: 296-305.), and (Concise Review: Isolation and Characterization of Cells from Human Term Placenta: Outcome of the First International Workshop on Placenta Derived Stem Cells").

In some aspects, trophoblasts are removed before cryopreservation or lyophilization.

ii. Macrophage Depletion or Devitalization

In some aspects, functional macrophages are selectively depleted or devitalized from the chorionic tissue. Surprisingly, macrophage depleted chorionic tissue has one or more of the following superior features: is substantially non-immunogenic; provides remarkable healing time; and provides enhanced therapeutic efficacy.

Functional macrophages can be removed in any suitable manner which substantially diminishes the macrophage content of the chorionic tissue. Optionally, the macrophages are selectively depleted or devitalized without eliminating a substantial portion of one or more therapeutic components from the chorionic tissue (e.g. MSCs, chorionic factors, etc.). Optionally, a majority (e.g. substantially all) of the macrophages are depleted or devitalized.

One method of selectively depleting immune cells such as macrophages comprises depleting or devitalizing the immune cells by rapid freezing rates such as 60-100° C./min. Although immune cells can be eliminated by rapid freezing rates, such a method can also be detrimental to therapeutic cells such as stromal cells (e.g. MSCs). Disclosed is a method of selectively depleting or devitalizing macrophages by refrigerating the chorionic tissue for a period of time (e.g. for at least about 10 min such as for about 30-60 mins) at a temperature above freezing (e.g. incubating at 2-8° C.) and then freezing the chorionic tissue (e.g. incubating at −80° C.±5° C.). Optionally, the step of freezing comprises freezing at a rate of less than 10°/min (e.g. less than about 5°/min such as at about 1°/min).

In some aspects, the step of refrigerating comprises soaking the chorionic tissue in a cryopreservation medium for a period of time sufficient to allow the cryopreservation medium to penetrate (e.g. equilibrate with) the chorionic tissue. In some aspects, the cryopreservation solution used in the methods disclosed herein can comprise DMSO and/or glycerol. In some aspects, the cryopreservation solution does not comprise DMSO or glycerol. Optionally, the step of freezing comprises reducing the temperature at a rate of about 1°/min. Optionally, the step of freezing comprises freezing at a rate of less than 10°/min (e.g. less than about 5°/min such as at about 1°/min).

In some aspects, the step of refrigerating comprises soaking the chorionic tissue in a cryopreservation solution at a temperature of about −10-15° C. (e.g. at 2-8° C.) for at least about any of: 10 min, 20 min, 30 min, 40 min, or 50 min. In another embodiment, the step of refrigerating comprises soaking the chorionic tissue in a cryopreservation medium (e.g. containing DMSO) at a temperature of about −10-15° C. (e.g. at 2-8° C.) for about any of: 10-120, 20-90 min, or 30-60 min. Optionally, the step of freezing comprises freezing at a rate of less than 10°/min (e.g. less than about 5°/min such as at about 1°/min).

iii. Removal of Maternal Blood Cells

In some aspects, maternal blood cells from vascularized tissue are depleted or removed from the placental product. Surprisingly, chorionic tissue depleted of maternal blood cells has one or more of the following superior features: is substantially non-immunogenic; provides remarkable healing time; and provides enhanced therapeutic efficacy.

Maternal blood cells can be removed in any suitable manner which substantially diminishes such cell content of the chorionic tissue. Optionally, the maternal blood cells are selectively removed or otherwise removed without eliminating a substantial portion of one or more therapeutic components from the chorionic tissue (e.g. MSCs, chorionic factors, etc.).

In some aspects, removal of maternal blood cells comprises separating the chorion from the placenta by cutting around the placental skirt on the side opposite of the UC. The chorion on the umbilical side of the placenta is not removed due to the vascularization on this side.

In some aspects, removal of maternal blood cells comprises rinsing the chorionic membrane (e.g. with buffer such as PBS) to remove gross blood clots and any excess blood cells.

In some aspects, removal of maternal blood cells comprises treating the chorionic membrane with an anticoagulant (e.g. citrate dextrose solution).

In some aspects, removal of maternal blood cells comprises separating the chorion from the placenta by cutting around the placental skirt on the side opposite of the UC and rinsing the chorionic membrane (e.g. with buffer such as PBS) to remove gross blood clots and any excess blood cells.

In some aspects, removal of maternal blood cells comprises separating the chorion from the placenta by cutting around the placental skirt on the side opposite of the UC and treating the chorionic membrane with an anticoagulant (e.g. citrate dextrose solution).

In some aspects, removal of maternal blood cells comprises separating the chorion from the placenta by cutting around the placental skirt on the side opposite of the UC, rinsing the chorionic membrane (e.g. with buffer such as PBS) to remove gross blood clots and any excess blood cells, and treating the chorionic membrane with an anticoagulant (e.g. citrate dextrose solution).

2. Preparing a Homogenized or Non-Homogenized Amniotic Matrix

Amniotic matrix for use in the disclosed methods and compositions can be prepared by homogenization. Homogenization can include, but is not limited to, those techniques that make the amniotic tissue uniform and identical throughout. Thus, homogenization can include blending, crushing dried or frozen tissue using a mortar and pestle, milling at room temperature, milling while frozen (a.k.a cryomilling), and using a tissue homogenizer. In some aspects, homogenized amniotic matrix is not decellularized. In some aspects, the homogenized amniotic matrix can be devitalized. Preparing an amniotic matrix can result in the amniotic matrices disclosed herein. In some aspects, amniotic matrix comprises only amniotic tissue and no other placental tissue or UC tissue.

In some aspects, the amniotic tissue for use in the disclosed methods and compositions is not homogenized and therefore can be a non-homogenized amniotic matrix. In some aspects, preparing a non-homogenized amniotic matrix can comprise mincing, dicing, chopping or digesting amniotic tissue to form a non-homogenized amniotic matrix.

In some aspects, homogenized or non-homogenized amniotic matrix can be made immunocompatible by selectively depleting it of functional immunogenic cells. An amnion, amniotic tissue, or amniotic matrix can be made immunocompatible by selectively removing immunogenic cells from the amnion relative to therapeutic cells. For example, immunogenic cells can be removed by depleting or devitalizing the immunogenic cells or by purification of amniotic tissue there from. In some aspects, making the amniotic tissue immunocompatible by selectively depleting it of functional immunogenic cells is performed by making sure the amnion is isolated from the remaining placental tissue. The removal of trophoblasts can be done by the methods described herein with regards to chorionic tissue or simply making sure the amnion is not associated with the chorion which comprises the trophoblast layer.

In some aspects, the selective depletion or devitalization of macrophages can be done by the methods described herein with regards to chorionic tissue.

In some aspects, the removal of maternal blood cells can be done by the methods described herein with regards to chorionic tissue.

3. Preparing a Homogenized or Non-Homogenized UC Matrix

UC matrix for use in the disclosed methods and compositions can be prepared by homogenization. Homogenization can include, but is not limited to, those techniques that make the UC tissue uniform and identical throughout. Thus, homogenization can include blending, crushing dried or frozen tissue using a mortar and pestle, milling at room temperature, milling while frozen, and using a tissue homogenizer. In some aspects, homogenized UC matrix is not decellularized. In some aspects, the homogenized UC matrix can be devitalized. Preparing an UC matrix can result in the UC matrices disclosed herein. In some aspects, UC matrix comprises only UC issue and no placental tissue.

In some aspects, the homogenized or non-homogenized UC matrix can comprise de-veined UC tissue. De-veining UC can be performed using techniques well known in the art. For example, an UC can be slit or cut longitudinally using, e.g., a scalpel and forceps, grooved director, or the like. This allows the UC membrane to be laid flat, allowing, e.g., removal of the Wharton's jelly, and/or one or more of the UC arteries, veins e.g., with a forceps. The UC membrane can also be processed further without cutting and opening the membrane. An UC vessel, for example, can be removed from the cord by grasping the vessels with a forceps and gently pulling and massaging until the vessel is removed, leaving the UC membrane as an intact tube. In a preferred embodiment of deveining, the umbilical vein of an UC can be canalized using the blunt probe of a vein stripper. The blunt probe can be replaced with a small bullet probe, and the vein can be tied to the probe with thread. The stripper can then be removed, and the process can be repeated with the umbilical arteries.

In some aspects, the UC tissue for use in the disclosed methods and compositions is not homogenized and therefore can be a non-homogenized UC matrix. In some aspects, preparing a non-homogenized UC matrix can comprise mincing, dicing, chopping or digesting UC tissue to form a non-homogenized amniotic matrix.

In some aspects, a UC matrix for use in the disclosed methods and compositions can be, but is not limited to, cut into pieces, pre-chilled, added to chilled-solution, dried in oven before cryomilling, etc. In some aspects, the UC matrix can be cut using scissors or minced into smaller pieces. In some aspects, the UC matrix can be cut using scissors or minced into smaller pieces prior to homogenizing (e.g. blending or milling).

In some aspects, during blending, the tissue (e.g. the UC or amniotic tissue) can be submerged in chilled saline or PBS to maintain cool temperatures during homogenization. If milling, the UC matrix or amniotic matrix can be dried prior to cutting/mincing or after cutting/mincing. In some aspects, drying can be done at room temperature, using a warm oven, or using a lyophilizer (no freezing required). In some aspects, once dried, the tissue can be placed into a milling device (either a grinding mill or a ball-bearing based mill, or other such mill) to be ground into small particles and homogenized. If cryomilling, the tissue can be dried or not dried first, frozen by storage in a freezer overnight (slow freeze) or by application of liquid nitrogen (flash freeze), and then milled in a cooled chamber.

In some aspects, an amniotic tissue and UC tissue can be combined as whole cord and membrane or as pre-cut/minced pieces prior to homogenization.

4. Combining the Non-Homogenized Chorionic Matrix, the Homogenized Amniotic Matrix, and the Homogenized UC Matrix In some aspects, non-homogenized chorionic matrix can be combined with a mixture of the homogenized amniotic matrix and the homogenized UC matrix. In some aspects, non-homogenized chorionic matrix can be combined with the homogenized amniotic matrix and then that combination can be combined with the homogenized UC matrix. In some aspects, non-homogenized chorionic matrix can be combined with the homogenized UC matrix and then that combination can be combined with the homogenized amniotic matrix. In some aspects, all of the non-homogenized chorionic matrix, homogenized amniotic matrix, and homogenized UC matrix can be combined simultaneously.

5. Isolating Amniotic Cells

In some aspects, the disclosed methods of making the disclosed compositions can further comprise, prior to preparing a homogenized or non-homogenized amniotic matrix, performing the step of isolating amniotic cells from the amniotic matrix.

Disclosed are methods of making the compositions disclosed herein comprising preparing a non-homogenized chorionic matrix, preparing a homogenized amniotic matrix, preparing a homogenized UC matrix, and combining the non-homogenized chorionic matrix, the non-homogenized chorionic matrix, and the homogenized UC matrix further comprising prior to preparing a homogenized amniotic matrix, performing the step of isolating amniotic cells from the amniotic matrix.

Disclosed are methods of making the compositions disclosed herein comprising preparing a non-homogenized chorionic matrix, preparing a homogenized amniotic matrix, preparing a homogenized UC matrix, and combining the non-homogenized chorionic matrix, the homogenized amniotic matrix, and the homogenized UC matrix further comprising prior to preparing a homogenized amniotic matrix, performing the step of isolating amniotic cells from the amniotic matrix and further comprising combining the isolated amniotic cells to the combined non-homogenized chorionic matrix, the homogenized amniotic matrix, and the homogenized UC matrix.

Thus, disclosed are methods of making the compositions disclosed herein comprising preparing a non-homogenized chorionic matrix, isolating amniotic cells from an amniotic tissue sample, preparing a homogenized amniotic matrix, preparing a homogenized UC matrix, and combining the non-homogenized chorionic matrix, the homogenized amniotic matrix, and the homogenized UC matrix.

Disclosed are methods of making the compositions disclosed herein comprising preparing a non-homogenized chorionic matrix, preparing a non-homogenized amniotic matrix, preparing a homogenized UC matrix, and combining the non-homogenized chorionic matrix, the non-homogenized amniotic matrix, and the homogenized UC matrix and further comprising, prior to preparing a non-homogenized amniotic matrix, performing the step of isolating amniotic cells from the amniotic matrix. In some aspects of the disclosed methods it can be unnecessary to isolate amniotic cells from the amniotic tissue prior to preparing a non-homogenized amniotic matrix. In some aspects, the disclosed methods can further comprise combining the isolated amniotic cells to the combined non-homogenized chorionic matrix, the non-homogenized amniotic matrix, and the homogenized UC matrix.

Disclosed are methods of making the compositions disclosed herein comprising preparing a non-homogenized chorionic matrix, preparing a non-homogenized amniotic matrix, preparing a non-homogenized UC matrix, and combining the non-homogenized chorionic matrix, the non-homogenized amniotic matrix, and the non-homogenized UC matrix and further comprising, prior to preparing a non-homogenized amniotic matrix, performing the step of isolating amniotic cells from the amniotic matrix. In some aspects of the disclosed methods it can be unnecessary to isolate amniotic cells from the amniotic tissue prior to preparing a non-homogenized amniotic matrix. In some aspects, the disclosed methods can further comprise combining the isolated amniotic cells to the combined non-homogenized chorionic matrix, the non-homogenized amniotic matrix, and the non-homogenized UC matrix.

Disclosed are methods of making the compositions disclosed herein comprising preparing a non-homogenized chorionic matrix, preparing a homogenized amniotic matrix, preparing a non-homogenized UC matrix, and combining the non-homogenized chorionic matrix, the homogenized amniotic matrix, and the non-homogenized UC matrix and further comprising, prior to preparing a non-homogenized amniotic matrix, performing the step of isolating amniotic cells from the amniotic matrix. In some aspects, the disclosed methods can further comprise combining the isolated amniotic cells to the combined non-homogenized chorionic matrix, the homogenized amniotic matrix, and the non-homogenized UC matrix.

In some aspects, the isolated amniotic cells from amniotic tissue are isolated from the same amniotic tissue used to prepare a homogenized or non-homogenized amniotic matrix. In some aspects, the isolated amniotic cells from amniotic tissue are isolated from a different amniotic tissue used to prepare a homogenized or non-homogenized amniotic matrix.

In some aspects, amniotic cells can be isolated from amniotic tissue using known enzymatic or mechanical methods, such as treatment with an enzyme solution and/or mechanical scraping of the epithelial surface using commercially available cell scrapers. For example, amniotic stromal cells, either fibroblasts or MSCs, can be isolated from amniotic tissue using known enzymatic or mechanical methods.

In some aspects, isolated epithelial or stromal cells from amniotic tissue can be present in small clusters of two or more cells still connected by cell-cell junction proteins or extracellular matrix proteins, or as single cells.

The viable, isolated amniotic cells from amniotic tissue can be added to the non-homogenized chorionic matrix.

D. Methods of Making Compositions

Disclosed are methods of making one of the compositions disclosed herein comprising isolating chorionic tissue, isolating amniotic tissue, isolating and deveining UC tissue, rinsing each of the isolated chorionic tissue, isolated amniotic tissue, and deveined UC tissue individually, mincing or digesting the isolated chorionic tissue, combining and homogenizing the isolated amniotic tissue and the deveined UC tissue to form a placental matrix, and combining the minced or digested (i.e. non-homogenized) chorionic tissue with the placental matrix.

Disclosed are methods of making one of the compositions disclosed herein comprising isolating chorionic tissue, isolating amniotic tissue, isolating and deveining UC tissue, rinsing each of the isolated chorionic tissue, isolated amniotic tissue, and deveined UC tissue individually, mincing or digesting the isolated chorionic tissue, mincing or digesting the isolated amniotic tissue; homogenizing the deveined UC tissue; combining the minced or digested (i.e. non-homogenized) amniotic tissue and the homogenized UC tissue to form a placental matrix, and combining the minced or digested chorionic tissue with the placental matrix.

Disclosed are methods of making one of the compositions disclosed herein comprising isolating chorionic tissue, isolating amniotic tissue, isolating and deveining UC tissue, rinsing each of the isolated chorionic tissue, isolated amniotic tissue, and deveined UC tissue individually, mincing or digesting the isolated chorionic tissue, mincing or digesting the isolated amniotic tissue; mincing or digesting the deveined UC tissue; combining the non-homogenized amniotic tissue and the non-homogenized UC tissue to form a placental matrix, and combining the minced or digested chorionic tissue with the placental matrix.

Disclosed are methods of making one of the compositions disclosed herein comprising isolating chorionic tissue, isolating amniotic tissue, isolating and deveining UC tissue, rinsing each of the isolated chorionic tissue, isolated amniotic tissue, and deveined UC tissue individually, mincing or digesting the isolated chorionic tissue, homogenizing the isolated amniotic tissue; mincing or digesting the deveined UC tissue; combining the homogenized amniotic tissue and the non-homogenized UC tissue to form a placental matrix, and combining the minced or digested chorionic tissue with the placental matrix.

In some aspects, the chorionic tissue and amniotic tissue can be derived from the same donor. In some aspects, the chorionic tissue and UC tissue can be derived from the same donor. In some aspects, the amniotic tissue and UC tissue can be derived from the same donor. In some aspects, the chorionic tissue, amniotic tissue and UC tissue can be derived from the same donor. In some aspects, each of the chorionic tissue, amniotic tissue and UC tissue can be derived from different donors. In some aspects, at least one of chorionic tissue, amniotic tissue and UC tissue is from a different donor than the other two tissues.

1. Isolating Chorionic Tissue

Isolating chorionic tissue can be performed using techniques well known in the art. In some aspects, isolating chorionic tissue includes separating the chorion from the remaining placental tissue. Thus, in some aspects, chorionic tissue only comprises the chorion or portions thereof.

In some aspects, isolating chorionic tissue includes depleting the chorionic tissue of immunogenic cells and factors. This can be done using the methods described herein.

1. Isolating Amniotic Tissue

Isolating amniotic tissue can be performed using techniques well known in the art. In some aspects, isolating amniotic tissue includes separating the amnion from the remaining placental tissue. Thus, in some aspects, amniotic tissue only comprises the amnion or portions thereof.

In some aspects, isolating amniotic tissue includes depleting the amniotic tissue of immunogenic cells and factors. This can be done using the methods described herein.

2. Isolating and Deveining UC Tissue

Isolating and deveining UC tissue can be performed using techniques well known in the art and those disclosed herein.

3. Rinsing

Each of the individual tissues (i.e. chorionic, amniotic, UC) can be rinsed. In some aspects, rinsing can include rinsing with a saline solution. In some aspects, rinsing can include a red cell lysis solution. In some aspect, rinsing can include a solution with an antibiotic.

In some aspects, rinsing can be for the sole purpose of cleaning each of the tissues and removing any excess components that are not part of the specific tissue sample. For example, rinsing can remove blood clots.

4. Mincing or Digesting the Isolated Chorionic Tissue

In order to keep as many cells viable as possible, the isolated chorionic tissue is handled delicately and not homogenized. In some aspects, the isolated chorionic tissue can be minced or digested.

Minced or digested chorionic tissue can result in the chorionic matrices disclosed herein. For example, mincing or digesting the isolated chorionic tissue results in a chorionic matrix with at least 30%, 40%, 50%, 60%, 70%, 80%, 90%, or 95% native, viable cells.

5. Combining Amniotic Tissue and UC Tissue to Form a Placental Matrix

In some aspects, isolated amniotic tissue and UC tissue can be homogenized to form an amniotic matrix and UC matrix, respectively. In some aspects, the amniotic tissue and UC tissue can be combined and then homogenized together to form a placental matrix. In some aspects, the amniotic tissue is homogenized to an amniotic matrix and the UC tissue is homogenized to an UC matrix and then the matrices are combined together to form a placental matrix. Thus, a placental matrix can be the combination of homogenized amniotic tissue and UC tissue.

In some aspects, homogenizing the isolated amniotic tissue and the deveined UC tissue to form a placental matrix comprises blending or milling the amniotic tissue and the deveined UC tissue together. In some aspects, any known homogenization technique can be used.

In some aspects, one or both of the isolated amniotic tissue and UC tissue can be non-homogenized to form an amniotic matrix and UC matrix, respectively.

In some aspects, the amniotic tissue and UC tissue can be combined and then homogenized together to form a placental matrix. In some aspects, the amniotic tissue can be minced, diced, chopped or digest into an amniotic matrix and the UC tissue can be homogenized to an UC matrix and then the matrices can be combined together to form a placental matrix. In some aspects, the amniotic tissue can be homogenized to an amniotic matrix and the UC tissue can be minced, diced, chopped or digest into to an UC matrix and then the matrices are combined together to form a placental matrix. In some aspects, a placental matrix can be the combination of non-homogenized amniotic tissue and homogenized UC tissue, homogenized amniotic tissue and non-homogenized UC tissue, or non-homogenized amniotic tissue and non-homogenized UC tissue.

In some aspects, the placental matrix can comprise viable and dead cells. In some aspects, the placental matrix is not decellularized. In some aspects, less than 50%, 40%, 30%, 20%, 10%, or 5% of the cells are viable in the placental matrix.

6. Combining the Minced or Digested Chorionic Tissue with the Placental Matrix In some aspects, the minced or digested chorionic tissue can be combined with the placental matrix. In some aspects, the combined minced or digested chorionic tissue with the placental matrix can comprise viable chorionic cells. In some aspects, 50%, 60%, 70%, 80%, 90% or 95% of the viable cells are native chorionic cells.

7. Isolating Epithelial Cells

In some aspects, the disclosed methods of making the disclosed compositions can further comprise, prior to preparing a homogenized or non-homogenized amniotic matrix, performing the step of isolating amniotic cells from the amniotic matrix.

Disclosed are methods of making one of the compositions disclosed herein comprising isolating chorionic tissue, isolating amniotic tissue, isolating and deveining UC tissue, rinsing each of the isolated chorionic tissue, isolated amniotic tissue, and deveined UC tissue individually, mincing or digesting the isolated chorionic tissue, combining and homogenizing the isolated amniotic tissue and the deveined UC tissue to form a placental matrix, and combining the minced or digested chorionic tissue with the placental matrix, further comprising isolating amniotic cells from the amniotic tissue prior to combining and homogenizing the isolated amniotic tissue and the deveined UC tissue to form a placental matrix and combining the isolated amniotic cells. In some aspects, the combining the isolated amniotic cells can occur after combining and homogenizing the isolated amniotic tissue and the deveined UC tissue to form a placental matrix. In some aspects, the combining the isolated amniotic cells can occur to the minced or digested chorionic tissue before combining the chorionic tissue with the placental matrix.

Disclosed are methods of making one of the compositions disclosed herein comprising isolating chorionic tissue, isolating amniotic tissue, isolating and deveining UC tissue, rinsing each of the isolated chorionic tissue, isolated amniotic tissue, and deveined UC tissue individually, mincing or digesting the isolated chorionic tissue, mincing or digesting the isolated amniotic tissue, homogenizing the deveined UC tissue, combining the non-homogenized amniotic tissue and homogenized UC tissue to form a placental matrix, and combining the minced or digested chorionic tissue with the placental matrix, further comprising isolating amniotic cells from the amniotic tissue prior to mincing or digesting the amniotic tissue and combining the isolated amniotic cells. In some aspects, the combining the isolated amniotic cells can occur after combining the non-homogenized amniotic tissue and homogenized UC tissue to form a placental matrix. In some aspects, the combining the isolated amniotic cells can occur to the minced or digested chorionic tissue before combining the chorionic tissue with the placental matrix.

Disclosed are methods of making one of the compositions disclosed herein comprising isolating chorionic tissue, isolating amniotic tissue, isolating and deveining UC tissue, rinsing each of the isolated chorionic tissue, isolated amniotic tissue, and deveined UC tissue individually, mincing or digesting the isolated chorionic tissue, combining and then mincing or digesting the isolated amniotic tissue and the deveined UC tissue to form a placental matrix, and combining the minced or digested chorionic tissue with the placental matrix, further comprising isolating amniotic cells from the amniotic tissue prior to combining and mincing or digesting the amniotic tissue and UC tissue to form a placental matrix and combining the isolated amniotic cells. In some aspects, the combining the isolated amniotic cells can occur after combining and mincing or digesting the isolated amniotic tissue and the deveined UC tissue to form a placental matrix. In some aspects, the combining the isolated amniotic cells can occur to the minced or digested chorionic tissue before combining the chorionic tissue with the placental matrix.

Disclosed are methods of making one of the compositions disclosed herein comprising isolating chorionic tissue, isolating amniotic tissue, isolating and deveining UC tissue, rinsing each of the isolated chorionic tissue, isolated amniotic tissue, and deveined UC tissue individually, mincing or digesting the isolated chorionic tissue, homogenizing the isolated amniotic tissue, mincing or digesting the deveined UC tissue, combining the homogenized amniotic tissue and non-homogenized UC tissue to form a placental matrix, and combining the minced or digested chorionic tissue with the placental matrix, further comprising isolating amniotic cells from the amniotic tissue prior to homogenizing the amniotic tissue and combining the isolated amniotic cells. In some aspects, the combining the isolated amniotic cells can occur after combining the homogenized amniotic tissue and non-homogenized UC tissue to form a placental matrix. In some aspects, the combining the isolated amniotic cells can occur to the minced or digested chorionic tissue before combining the chorionic tissue with the placental matrix.

8. Lyophilizing

The disclosed methods of making a composition comprising a non-homogenized chorionic matrix, a homogenized or non-homogenized amniotic matrix and a homogenized or non-homogenized UC matrix, wherein the non-homogenized chorionic matrix comprises viable cells can further comprise lyophilizing the combined chorionic tissue and placental matrix. In some aspects, each of the components of the disclosed compositions can be lyophilized separately and then mixed together. In some aspects, one or more of the components of the disclosed compositions can be lyophilized together. In some aspects, each of the non-homogenized chorionic matrix, homogenized or non-homogenized amniotic matrix, homogenized or non-homogenized UC matrix and isolated amniotic cells can be lyophilized separately. In some aspects, after lyophilizing each component separately, each can then be combined together.

Any known lyophilization technique and equipment can be used. In some aspects, methods of lyophilizing the disclosed compositions can comprise contacting one of the disclosed compositions with a lyoprotectant solution, freezing the composition, performing a first drying step of the composition after freezing, and performing a second drying step of the composition after the first drying step.

In some aspects, methods of lyophilizing the disclosed compositions can comprise contacting one of the disclosed compositions with a lyoprotectant solution, freezing the composition, performing a first drying step of the composition after freezing, and performing a second drying step of the composition after the first drying step, and further comprising a step of reconstituting the lyophilized tissue.

In some aspects, contacting the composition with a lyoprotectant solution can include a short or prolonged contact. In some aspects, the first drying step of the composition after freezing occurs between −45° C. and −15° C. In some aspects, the second drying step can be carried out at a temperature that is greater than the temperature of the freezing step. In some aspects, the second drying step can be carried out at a temperature that is greater than the temperature of the freezing step and the first drying step.

E. Methods of Treating

Disclosed are methods of treating a tissue injury or chronic pain comprising administering any of the disclosed compositions to an area of a subject comprising a tissue injury. In some aspects, the tissue injury can be osteoarthritis, plantar fasciitis, carpal tunnel, tendonitis, synovitis, ruptured or torn Achilles tendon, critical limb ischemia, ulcers, pyoderma gangrenosum, epidermolysis bullosa, surgical adhesions, surgical applications or other wounds.

In some aspects, any of the disclosed compositions can be administered by injecting the composition to the area of a subject comprising a tissue injury or local region of chronic pain.

In some aspects, any of the disclosed compositions can be administered by applying the composition topically to an area of a subject comprising the tissue injury or chronic pain.

In some aspects, any of the disclosed compositions can be administered by implanting the composition to the area of a subject comprising a tissue injury.

In some aspects, the subject can be a mammal. In some aspects, the subject can be human.

EXAMPLES

FIGS. 1-4 provide examples of the platform building blocks and how they form compositions. They also show an example of a method of processing a placenta and umbilical cord in order to produce an example of one of the disclosed compositions.

Figures 5A, 5B, 5C, 5D, 5E, 5F, 5G, 5H:
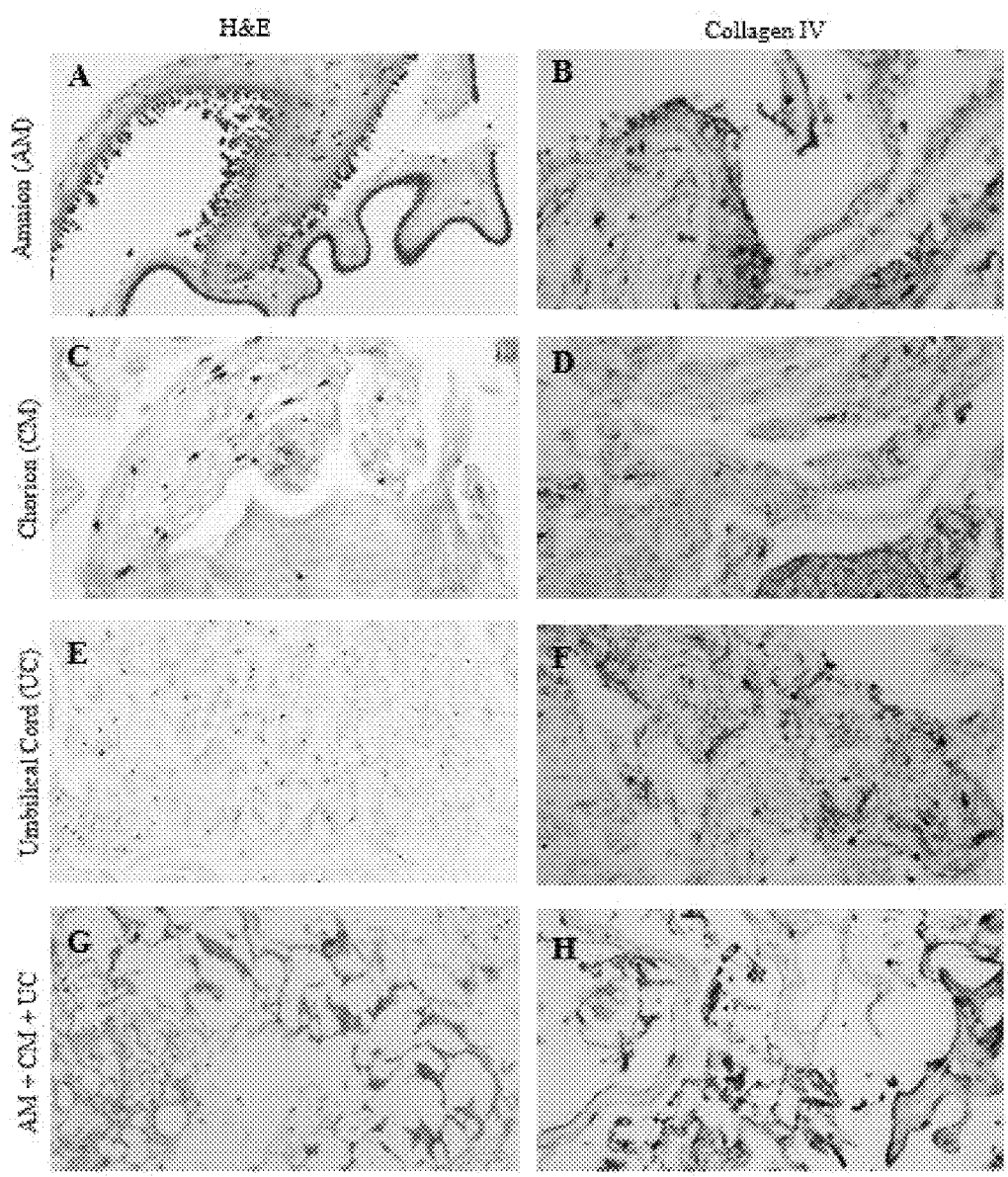
FIG. 5A, 5B, 5C, 5D, 5E, 5F, 5G, and 5H depict the histological appearance of the individual placental tissues and the final compositions containing viable non-homogenized chorionic components and homogenized placental matrix. A) amnion, H&E stain; B) amnion; Collagen IV stain; C) chorion, H&E stain; D) chorion; Collagen IV stain; E) umbilical cord, H&E stain; F) umbilical cord; Collagen IV stain; G) amnion+chorion+umbilical cord, H&E stain; H) amnion+chorion+umbilical cord; Collagen IV stain.

FIG. 5 shows the histological appearance of compositions. Representative pictures of H&E-stained sections of (A) Amnion (C) Chorion (E) Umbilical cord (G) the viable compositions (AM+CM+UC). Representative pictures of Collagen IV stained sections of (B) Amnion (D) Chorion (F) Umbilical cord (H) the viable compositions (AM+CM+UC). All images were taken at 20× magnification.

Figure 6:
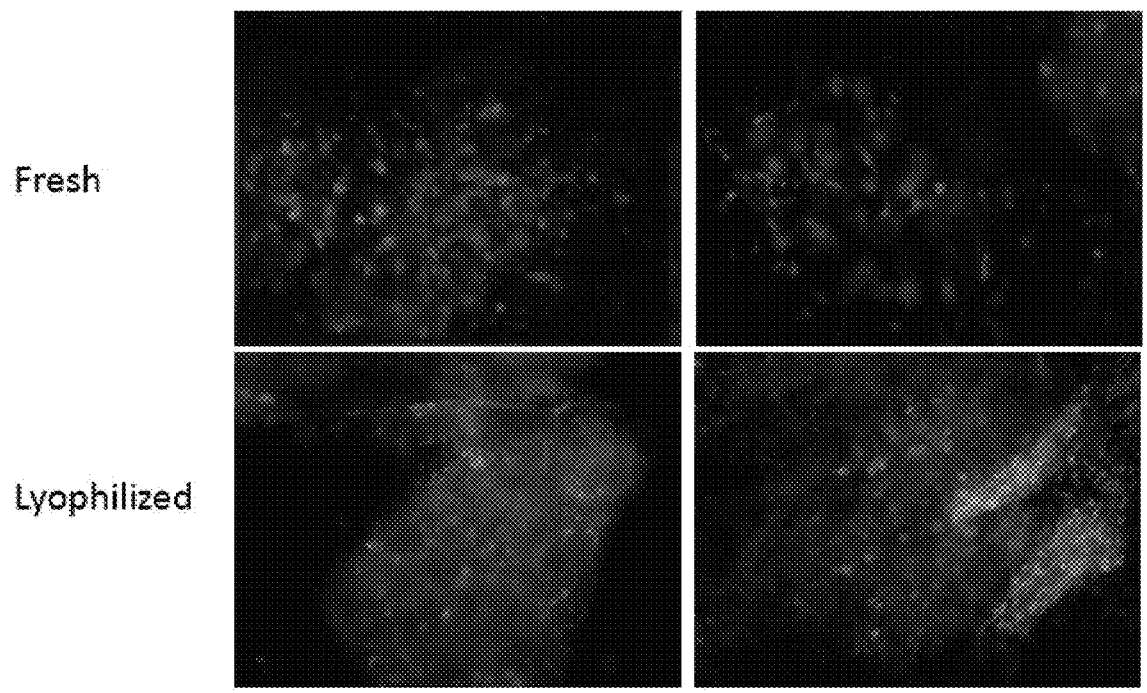
FIG. 6 shows the high cell viability of the non-homogenized chorionic components of compositions before and after preservation by lyophilization.

FIG. 6 shows cell viability of the non-homogenized chorionic component of the compositions after mincing, both fresh and after preservation by lyophilization. All samples were treated with the same solutions and lyophilized in the same manner. Each group was processed from the same starting material and represents samples taken in succession during a mincing process. Cell viability of the lyophilized group was nearly equivalent ~90% of the starting material viability, and estimated to be 80-85% total cell viability for both groups.

Figure 7:
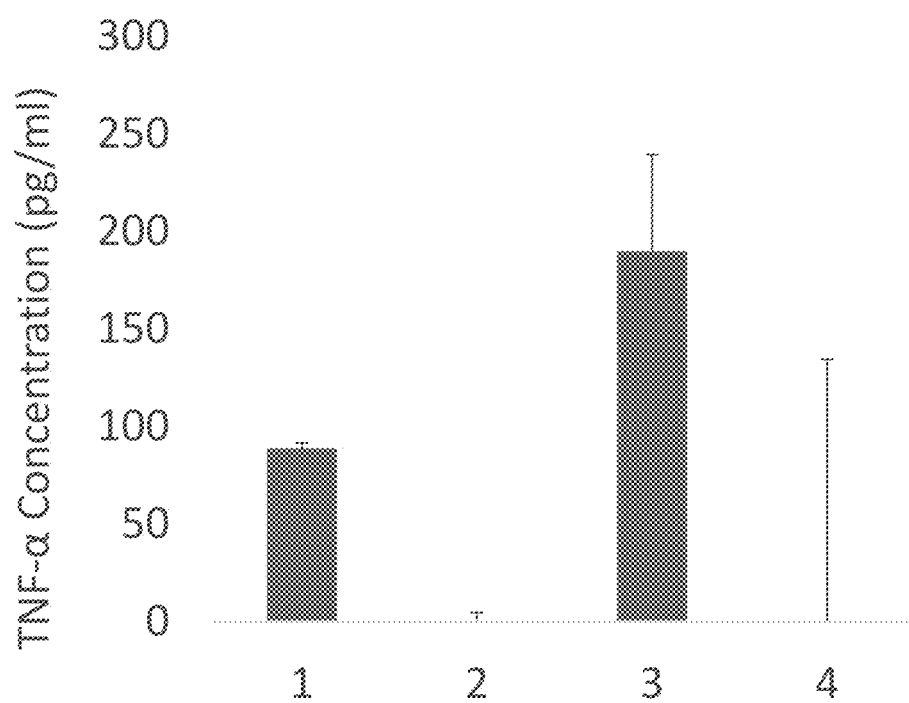
FIG. 7 demonstrates the lack of an immunogenic response to the compositions due to the selective depletion or devitalization of immunogenic cell types.

FIG. 7 demonstrates the lack of an immune response exhibited by the compositions, which is a result of the selective depleting or devitalizing of immunogenic cell types (lymphocytes, macrophages, endothelial cells, etc.) during the cryopreservation and/or lyophilization processes.

FIG. 8 is a table summarizing the FACS analysis of cells isolated from the non-homogenized viable chorionic component of the compositions for one lot. As shown, the cells are all negative (<5% positive) for markers of immunogenic cell types (CD45, CD31, HLA-DR) and the majority of cells (>50%) are also positive for cell surface markers typical of MSCs (CD90, CD73, CD44, HLA-ABC). This demonstrates the presence of viable chorionic stem cells in the compositions.

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

Those skilled in the art will recognize, or be able to ascertain using no more than routine experimentation, many equivalents to the specific embodiments of the method and compositions described herein. Such equivalents are intended to be encompassed by the following claims.

We claim:

1. A composition comprising a non-homogenized chorionic matrix, a devitalized homogenized amniotic matrix, and a devitalized homogenized umbilical cord (UC) matrix, wherein the non-homogenized chorionic matrix comprises native cells, wherein the composition is lyophilized, and wherein at least 70% of the native cells of the non-homogenized chorionic matrix are viable after storage at room temperature in the lyophilized state, and wherein the native cells are not culturally expanded after lyophilization.

2. The of claim 1, further comprising a viscous modifier.

3. The composition of claim 1 further comprising viable, isolated amniotic cells.

4. The composition of claim 1, further comprising a scaffold.

5. The composition of claim 1, wherein the homogenized amniotic matrix and/or the homogenized UC matrix are not decellularized.

6. The composition of claim 1, wherein the non-homogenized chorionic matrix is minced.

7. The composition of claim 1, wherein the composition comprises viable chorionic stem cells, amniotic stem cells, fibroblasts, epithelial cells or a combination thereof.

8. The composition of claim 1, wherein the homogenized amniotic matrix and homogenized UC matrix are derived from the same donor.

9. The composition of claim 1, wherein the nonhomogenized chorionic matrix and homogenized amniotic matrix are from the same donor.

10. The composition of claim 1, wherein the nonhomogenized chorionic matrix and homogenized UC matrix are from the same donor.

11. The composition of claim 1, wherein the homogenized UC matrix comprises de-veined UC tissue.

12. A pharmaceutical composition comprising the composition of claim 1 and a pharmaceutically acceptable carrier.

\* \* \* \* \*